US005856446A

United States Patent [19]
Weiner et al.

[11] Patent Number: 5,856,446
[45] Date of Patent: Jan. 5, 1999

[54] METHOD OF TREATING RHEUMATOID ARTHRITIS WITH LOW DOSE TYPE II COLLAGEN

[75] Inventors: Howard L. Weiner, Brookline; David A. Hafler, West Newton; David E. Trentham, North Quincy, all of Mass.

[73] Assignee: Autoimmune Inc., Lexington, Mass.

[21] Appl. No.: 675,886

[22] Filed: Jul. 5, 1996

Related U.S. Application Data

[60] Provisional application No. 60/000,964 Jul. 7, 1995.
[51] Int. Cl.⁶ .................................................. A61K 38/17
[52] U.S. Cl. .......................................... 530/356; 514/885
[58] Field of Search ......................... 424/184.1; 530/356

[56] References Cited

U.S. PATENT DOCUMENTS

| | | | |
|---|---|---|---|
| 3,561,444 | 2/1971 | Boucher | 128/194 |
| 3,703,173 | 11/1972 | Dixon | 128/194 |
| 4,309,404 | 1/1982 | DeNeale et al. | 424/21 |
| 4,309,406 | 1/1982 | Guley et al. | 424/21 |
| 4,556,552 | 12/1985 | Porter et al. | 424/32 |
| 4,624,251 | 11/1986 | Miller | 128/200.14 |
| 4,635,627 | 1/1987 | Gam | 128/200.14 |
| 4,659,696 | 4/1987 | Hirai et al. | 514/15 |
| 4,695,459 | 9/1987 | Steinman et al. | 424/95 |
| 4,698,332 | 10/1987 | Ogasawara et al. | 514/42 |
| 4,804,745 | 2/1989 | Koepff et al. | 530/356 |
| 4,863,720 | 9/1989 | Burghart et al. | 424/45 |
| 4,883,784 | 11/1989 | Kaneko | 514/8 |
| 5,075,112 | 12/1991 | Lane | 424/434 |
| 5,194,425 | 3/1993 | Sharma et al. | 514/8 |
| 5,276,013 | 1/1994 | Conrad et al. | 514/2 |
| 5,284,935 | 2/1994 | Clark et al. | 530/403 |
| 5,399,347 | 3/1995 | Trentham et al. | 424/184.1 |

FOREIGN PATENT DOCUMENTS

| | | |
|---|---|---|
| 0 272 097 | 6/1988 | European Pat. Off. . |
| 0 304 279 | 2/1989 | European Pat. Off. . |
| 0 271 577 | 10/1995 | European Pat. Off. . |
| WO 80/02501 | 11/1980 | WIPO . |
| WO 88/10120 | 12/1988 | WIPO . |
| WO 91/08760 | 6/1991 | WIPO . |
| WO 92/06704 | 4/1992 | WIPO . |
| WO 92/06708 | 4/1992 | WIPO . |
| WO 93/026990 | 2/1993 | WIPO . |
| WO 93/16724 | 9/1993 | WIPO . |
| WO 93/21222 | 10/1993 | WIPO . |

OTHER PUBLICATIONS

AutoImmune Press Release of May 12, 1997.
Allegretta et al., *Science*, 247:718, 1990.
Al–Sabbagh et al., *Neurology*, 42:346, 1992.
Alvord et al., *Annals of Neurol.*, 6:461, 1979.
Alvord et al., *Annals of Neurol.*, 6:469, 1979.
Alvord et al., *Annals of Neurol.*, 6:474,1979.
Alvord et al., *Ann. N.Y. Acad. Sci.*, 122:333, 1965.
Avrilionis et al., *J. Neuroimmunol.*, 35:201, 1991.
Barker et al., *Clin. Exp. Immunol.*, 85:33, 1991.
Belik et al., *Vorp. Med. Khim.*, 24:372, 1978.
Ben–Nun et al., *J. Immunol.*, 129:303, 1982.
Bitar et al., *Cell Immunol.*, 112:364, 1988.
Bitar, Dissertation entitled *The Suppressive Effects of Oral Myelin . . .* , 1986.
Bradley–Mullen et al., *Cell Immunol.*, 39:289, 1978.
Bradley–Mullen et al., *Cell Immunol.*, 51:408, 1980.
Burns et al., *Neurology*, 36:92, 1986.
Burns et al., *J. Exp. Med.*, 169:27, 1989.
Campbell et al., *Arch. Neurol.*, 29:10, 1973.
Carnegie et al., *Immunology*, 19:55, 1970.
Chen et al., *Science*, 265:1237, 1994.
Cremer et al., *J. Immunol.*, 131:2995, 1983.
DeHeer et al., *J. Immunol.*, 16:1051, 1976.
Eisenbarth, *New Eng. J. Med.*, 314:1360, 1986.
Englert et al., *Cell Immunol.*, 87:357, 1984.
Eylar, *Adv. Exp. Med. Bio.*, 98:259, 1978.
Eylar et al., *Nature*, 236:74, 1972.
Eylar et al., *Neurochem. Res.*, 4:249, 1979.
Friedman et al., *Proc. Nat'l. Acad. Sci., USA*, 91:6688, 1994.
Fritz et al., *J. Immunol.*, 134:2328, 1985.
Fritz et al., *J. Immunol.*, 130:191, 1983.
Fritz et al., *J. Immunol.*, 130:1024, 1983.
Gaur et al., *Science*, 258:1491, 1992.
Gautam et al., *J. Immunol.*, 135:2975, 1985.
Gonsette et al., *J. Neurol.*, 216:27, 1977.
Harrison et al., *J. Clin. Invest.* 89:1161, 1992.
Hashim et al., *Arch. of Biochem. and Biophysics*, 156:287, 1973.
Higgins et al., *J. Immunol.*, 140:440, 1988.
Higgins et al., *J. Neuroimmunol.*, 16:77, 1987.
Higgins et al., *Annals of Neurol.*, 20:161, abstract P154, 1986.
Holoshitz et al., *J. Immunol.*, 131:2810, 1983.
Holoshitz et al., *Science*, 219:56, 1983.
Howell et al., *Science*, 246:668, 1989.
Janeway, *Nature*, 341:482, 1989.
Kagnoff, *Annals N.Y. Acad. Sci.*, pp. 248–265, 1982.
Kardys et al., *J. Immunol.*, 127:862, 1981.
Khoury et al., *J. Exp. Med.*, 176:1355, 1992.
Lando et al., *Nature*, 287:551, 1980.
Lando et al., *J. Immunol.*, 126:1526, 1981.
Lane et al., *Sharks Don't Get Cancer*, 1992.
Lider et al., *J. Immunol.*, 142:748, 1989.
Lider et al., *Ann. N.Y. Acad. Sci.*, 475:267, 1986.
Martin et al., *J. Immunol.*, 148:1359, 1992.
Martin et al., *J. Exp. Med.*, 173:19, 1991.
Martin et al., *J. Immunol.*, 145:540, 1990.
Mattingly et al., *J. Immunol.*, 125:1044, 1980.
McDermott et al., *J. Neurol. Sci.*, 46:137, 1980.
McKenna et al., *Cell Immunol.*, 81:391, 1983.
McKenna et al., *Cell Immunol.*, 88:251, 1984.

(List continued on next page.)

*Primary Examiner*—Theodore J. Criares
*Attorney, Agent, or Firm*—Darby & Darby

[57] ABSTRACT

A method for suppressing autoimmune response in an afflicted joint in a human. The method involves oral administration of between about 5 and 25 μg per day of type II collagen.

12 Claims, 5 Drawing Sheets

OTHER PUBLICATIONS

Michael, *Immunol. Invest.,* 18:1049, 1989.
Miller et al., *J. Exp. Med.,* 174:791, 1991.
Miller et al., *Proc. Nat'l. Acad. Sci., USA,* 89:421, 1992.
Miller, *FASEB,* 5:2560, 1991.
Miller et al., *J. Neuroimmunol.,* 39:243, 1992.
Miller et al., *J. Neuroimmunol.,* 46:73, 1993.
Miller et al., *J. Immunol.,* 151:7307, 1993.
Mokhtarian et al., *Nature,* 309:356, 1984.
Mori et al., *Diabetologia,* 29:244, 1986.
Mowat, *Immunol. Today,* 8:93, 1987.
Myers et al., *J. Exp. Med.,* 170:1999, 1989.
Myers et al., *J. Immunol.,* 143:3976, 1989.
Nagler–Anderson et al., *Proc. Nat'l., Acad. Sci. USA.,* 83:7443, 1986.
Nagler–Anderson, Dissertation entitled *Immunoregulation of an Expermental Model . . . ,* 1986.
Newman, *Aerosols and the Lung,* pp. 197–224, 1984.
Ngan et al., *J. Immunol.,* 120:861, 1987.
Nussenblatt et al., *J. Immunol.,* 144:1689, 1990.
Ota et al., *Nature,* 346:183, 1990.
Pette et al., *Proc. Nat'l. Acad. Sci.,* USA, 87:7968, 1990.
Pettinelli et al., *J. Immunol.,* 129:1209, 1982.
Phadke et al., *Arthritis and Rheumatism,* 27:797, 1984.
Pinals et al., *Arthritis Rheum.,* 24:1308, 1981.
Raine et al., *Lab. Invest.,* 48:275, 1983.
Rama et al., *Connective Tissue Research,* 12:111, 1984.
Raziuddin et al., *J. Immunol.,* 128:2073, 1982.
Richman et al., *J. Immunol.,* 121:2429, 1978.
Rothbard, *1st Forum in Virology,* pp. 518–527, 1986.
Salk et al., *Studies of Myelin Basic Protein . . . ,* 419–427, 1984.
Santos et al., *J. Immunol.,* 150:115A, 1993.
Schoen et al., *J. Immunol.,* 128:717, 1982.
Schwartz, *Ann. Rev. Immunol.,* 3:237, 1985.
Sewel et al., *The Lancet,* 341:283, 1993.
Sriram et al., *Cell Immunol.,* 75:378, 1983.
Steinbroker et al,. *JAMA,* 140:659, 1949.
Strejan et al., *Cell Immunol.,* 84:171, 1984.
Su et al., *J. Neuroimmunol.,* 34:181, 1991.
Swierkosz et al., *J. Immunol.,* 119:1501, 1977.
Thompson et al., *Clin. Exp. Immunol.,* 64:581, 1985.
Titus et al., *Int. Arch. Allergy Appl. Immunol.,* 65:323, 1981.
Traugott et al., *J. Neurol. Sci.,* 56:65, 1982,
Trentham et al., *J. Clin. Invest.,* 66:1109, 1980.
Trentham et al., *Science,* 261:1727, 1993.
Unanue et al., *Science,* 236:551, 1987.
Vandenbark et al., *Nature,* 341:541, 1989.
Weinblatt et al., *N. Eng. J. Med.,* 312:818, 1985.
Weiner et al., *Science,* 259:1321, 1993.
Weiner et al., *Neurology,* 39:172, 1989.
Wells, *J. Infect. Dis.,* 9:147, 1911.
Whitacre et al., *6th Int'l. Cong. Immunol.,* 1986.
Whitacre et al.,, *5th Int'l. Cong. Immunol.* 1983.
Whitacre et al., *J. Immunol.* 147:2155, 1991.
Whitaker, *J. Bio. Chem.,* 250:9106, 1975.
Williams et al., *Arthritis Rheum.,* 31:702, 1988.
Wucherpfenning et al., *Science,* 248:1016, 1990.
Yoon, *Science,* 259:1263, 1993.
Zamvil et al., *Nature,* 324:258, 1986.
Zhang et al., *FASEBJ,* 4:A3264), 1990.
Zhang et al., *Proc. Natl'l. Acad. Sci. USA,* 88:10252, 1991.
Zhang et al., *J. Immunol.,* 145:2489, 1990.
Zhang et al., *Arthritis Rheum,* 33:(abstract No. C10), 1990.
Zhang et al., *Arthritis Rheum.,* 33:(abstract No. C11), 1990.
Zhang et al., *FASEBJ.,* 6A1693, 1992.

METHOD OF TREATING RHEUMATOID ARTHRITIS WITH LOW DOSE TYPE II COLLAGEN

This application is a continuation of Provisional application No. 60/000,964 filed Jul. 7, 1995.

FIELD OF THE INVENTION

This invention pertains to treatment of autoimmune arthritis in humans. Specifically, the invention is directed to oral administration of a low dosage of type II collagen to humans to induce specific suppression of the autoimmune response involved in rheumatoid arthritis. The invention is also directed to oral dosage forms useful in the treatment of arthritis in humans comprising type II collagen.

BACKGROUND OF THE INVENTION

Collagen is the most common protein in the structural support of the human or mammalian body. Collagen's basic elemental unit is the tropocollagen protein. Tropocollagen is composed of three polypeptide chains of the same size. These chains are wound about each other forming a super-helical cable or a triple-stranded helical rod. Each of the three chains in tropocollagen consists of about a thousand amino acid residues.

Several different types of collagen proteins are currently recognized as distinct, differing in amino acid composition and length. Type I collagen is composed of two alpha-1(I) and one alpha-2 polypeptide chains. Type I collagen is mostly found in the supporting structure of skin tissue, tendon, bone and in the eye cornea. Type II collagen contains three polypeptide chains of the alpha-1(II) type and is found primarily in articular cartilage, within the intervertebral discs and in the vitreous body within the eye. Type III collagen is composed of three alpha-1(III) polypeptide chains and is found in tissues such as fetal skin, the cardiovascular system and reticular fibers in the eye. Type IV collagen has a mixture of two alpha-1(IV) and one alpha-2(IV) polypeptide chains and is primarily found in basement membranes. Type V collagen has two alpha-1(V) and one alpha-2(V) polypeptide chains and is found, e.g., in placenta and skin. Other types of collagen have comparable structural differences from one another.

Rheumatoid arthritis is a cell-mediated autoimmune disease, i.e., a condition where the immune system mistakenly perceives the body's own tissue as foreign and mounts an abnormal immune response against it. Rheumatoid arthritis is characterized by persistent inflammatory synovitis that causes destruction of cartilage and bone erosion, leading to structural deformities in the peripheral joints. Joints containing articular cartilage of which Type II collagen is a major component are particularly affected.

Rheumatoid arthritis is accompanied by joint swelling, inflammation, stiffness and pain especially upon flexing. In the advanced stages of arthritis, debilitating pain may result from even a slight movement of the joints. A substantial percentage of afflicted humans possess T-cells of the CD4+ type specifically reactive with collagen and/or have an abnormal humoral response against collagen.

Present treatment for arthritis involves use of nonspecific cytotoxic immunosuppressive drugs. These drugs suppress the entire immune system and are incapable of selectively suppressing the abnormal autoimmune response. This global restraint of the immune system over time increases the risk of infection. Non-limiting examples of such immunosuppressive drugs include methotrexate, cyclophosphamide, Imuran (azathioprine) and cyclosporin A.

Additionally, prolonged therapy with these nonspecific cytotoxic immunosuppressive drugs entails toxic side effects, including increased tendency towards development of certain malignancies, kidney failure, bone marrow suppression, diabetes and liver function disorders. Moreover, cytotoxic immunosuppressive drug therapy merely slows down the progress of the disease, which resumes at an accelerated pace after the therapy is discontinued. For example, about six weeks after such a drug is discontinued, the patient deteriorates to the same stage as before the treatment was begun. In addition, effectiveness of these drugs is self-limiting; they gradually cease being effective after about 2–5 years.

Steroid compounds such as prednisone and methylprednisolone (which are also non-specific immunosuppressive and antiinflammatory drugs) are also used for symptomatic relief. Steroids also have significant toxic side effects associated with their long term use.

Thus, current treatments for arthritis are of limited efficacy, involve significant toxic side effects, and cannot be used continuously for extended periods of time, which further limits their efficacy. Rheumatoid arthritis afflicts over 2 million individuals in the United States in any given year. Accordingly, there is an acute need for novel treatments and for novel therapeutic compositions for human rheumatoid arthritis that do not suffer from one or more of the drawbacks identified above.

An alternative treatment for arthritis is the oral antigen tolerization therapy proposed by the present inventors. It involves the oral administration of one or more tissue-specific antigens (i.e., antigens occurring only in the tissue under autoimmune attack) which have the ability to suppress the autoimmune response responsible for a particular autoimmune disease specifically, thus leaving other immune functions essentially intact.

The antigens useful in this approach generally include autoantigens, i.e., tissue-specific antigens that are themselves the subject of autoimmune attack. Pure bystander antigens, which are also tissue-specific (but are not the target of autoimmune attack) also possess the ability to elicit suppressor T-cells which are targeted to the afflicted tissue where they exert their immune suppressive activity via the release of immunoregulatory substances such as transforming growth factor-beta (TGF-$\beta$), interleukin-4, or interleukin-10. These immunoregulatory substances in turn down-regulate all immune cells concentrated in the vicinity of the afflicted tissue, thereby suppressing immune responses in that locality. Bystander antigens include without limitation portions of autoantigens that (i) are not themselves the target of autoimmune attack and (ii) possess the requisite suppressive activity via elicitation of suppressor T-cells, i.e. are recognized by T-cells of the host.

Prior to the work of the present inventors, oral antigen tolerance therapy for arthritis had been tried only on artificially induced arthritis-like diseases in animals (adjuvant arthritis and collage-induced arthritis).

In the rodent models, collagen was shown only to prevent disease induction and had no or minimal effect on pre-induced disease. Oral antigen tolerization had never been tried in humans afflicted with arthritis.

Weiner et al., U.S. Pat. No. 5,399,347 discloses the oral administration of between 50 $\mu$g and 10 mg and preferably between 100 $\mu$g to 500 $\mu$g per day of type II collagen, to treat arthritis in humans. At the time the invention of the '347 patent was made, 50 $\mu$g per day was considered to be an extraordinarily small quantity of active ingredient for administration to humans for effective treatment of rheumatoid arthritis. It has now been discovered that even more effective and improved treatment of humans suffering from rheumatoid arthritis is obtained by oral administration of as little as 5 and typically 10–25 μg per day, and preferably 20 μg per day of type II collagen.

The discovery that 20 μg of type II collagen per day is a more effective treatment for rheumatoid arthritis than higher doses is entirely surprising and unexpected. Classical pharmacology posits that a dose-response relationship exists whereby higher doses of a pharmacological agent give greater responses until a plateau is reached in the response. Lower doses should give lesser, not greater, responses. This would especially be expected to be the case with the present invention, which involves oral administration of a protein. Most pharmacological agents which are proteins must be administered via injection (e.g. insulin) because of the well-known destructive effects on proteins resulting from passage through the strongly acidic environment of the human digestive system. The finding that a lesser amount of orally administered type II collagen (on the order of 5 or 10 to 25 μg) was useful in treating rheumatoid arthritis was therefore entirely surprising and unexpected.

OBJECTS OF THE INVENTION

An object of the present invention is to provide a treatment for human autoimmune arthritis including without limitation rheumatoid arthritis.

Another object of the invention is to specifically suppress the abnormal immune response attacking cartilage and resulting in subchondral bone deterioration in human beings.

An additional object of the invention is to provide a clinical treatment for rheumatoid arthritis without undesirable side effects in human beings, such as one or more of those associated with conventional therapy.

A further object of the invention is to significantly reduce symptoms associated with arthritis such as one or more of swelling, inflammation, stiffness and pain of the joints in human beings.

Yet another object of the invention is to provide pharmaceutical formulations useful in the treatment of human rheumatoid arthritis.

A further object of the invention is a method of treating rheumatoid arthritis in humans by orally administering to a human in need of such treatment between 5 and 25 μg and preferably between 10 and 25 per day of type II collagen.

SUMMARY OF THE INVENTION

One or more of the foregoing objects are achieved in a therapeutic treatment for autoimmune arthritis in humans by providing pharmaceutical formulations and dosage forms for oral administration comprising collagen protein with or without a synergist in an effective amount and by providing methods for treating such arthritis comprising the oral administration to afflicted humans of said formulations in effective amounts.

DETAILED DESCRIPTION OF THE INVENTION

Figure 1:
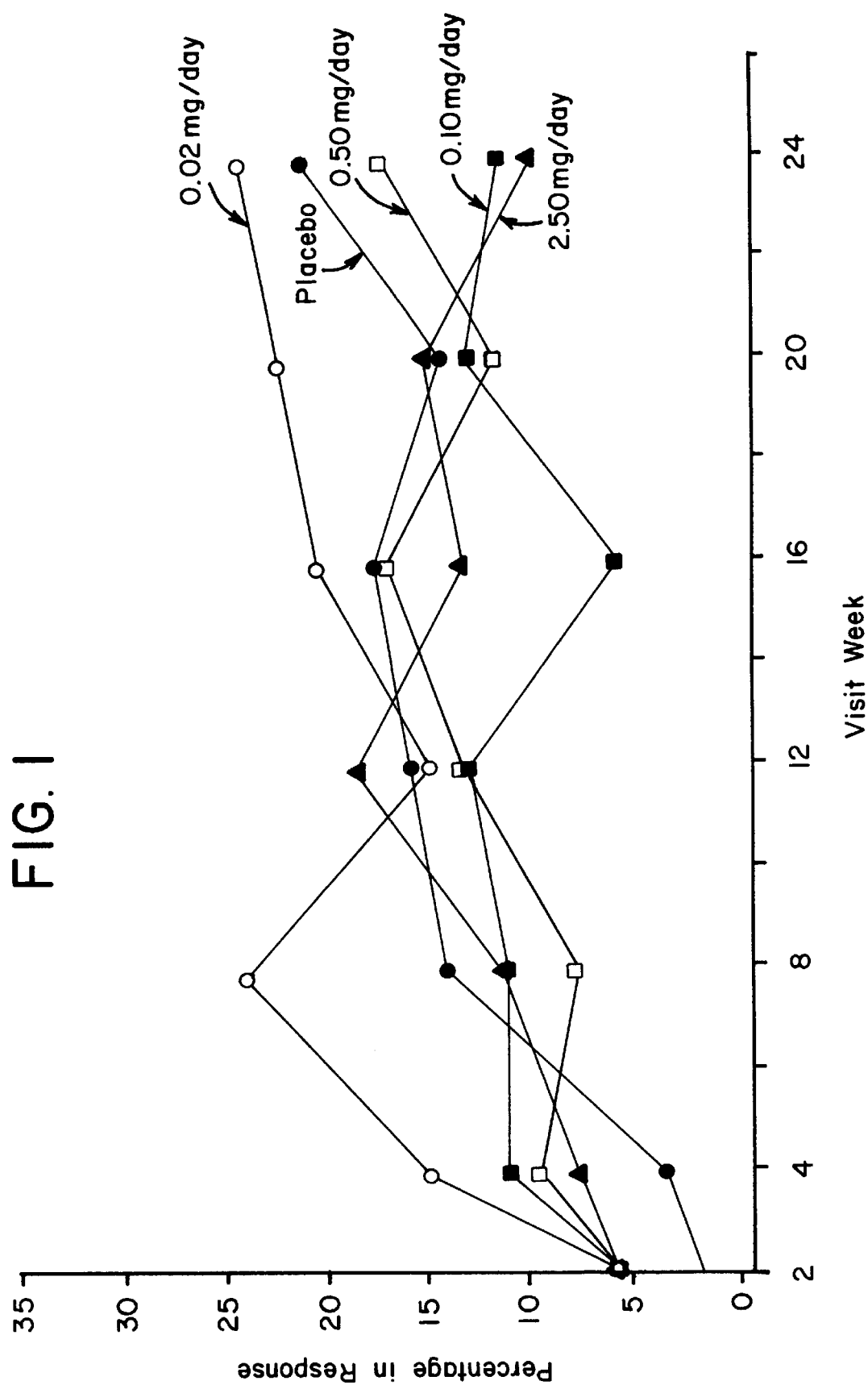
FIG. 1 is a graph which shows the percentage of subjects in response to treatment with a range of doses of type II collagen in the Intent-to-Treat population over a period of 24 weeks.

All patents, patent applications, and literature references cited in this specification are hereby incorporated by reference in their entirety. In case of inconsistency, the present description including the definitions and interpretations contained herein will prevail.

Definitions

Each of the following terms used in this specification shall have the meaning ascribed to it below:

"Treatment" includes both prophylactic measures to prevent the onset and appearance of arthritis as well as to prevent the onset and appearance of the abnormal immune response against the body's own cartilage involved in arthritis. The term also encompasses the suppression or mitigation of the abnormal (cell and/or humoral) immune response to the body's own collagen or more generally cartilage as well as the alleviation, arrest, or elimination of clinical symptoms after the onset (i.e., clinical manifestation) of autoimmune arthritis.

"Mammal" is any organism having an immune system and being susceptible to an autoimmune disease. This term encompasses human beings.

"Autoimmune disease" is defined as a malfunction of the immune system of mammals, in which the immune system fails to distinguish between foreign substances within the mammal and/or autologous tissues or substances within the mammal and/or autologous tissues or substances and, as a result, treats autologous tissues and substances as if they were foreign and mounts an immune response against them.

A T-cell mediated, or T-cell dependent autoimmune disease is a disease that is either mediated by immune attack by T-cells or which has a T-cell component. In either case the disease is characterized by inflammation of the afflicted organ or tissue.

"Synergists" are defined as substances which augment or enhance the suppression of the clinical and/or histological manifestation of arthritis when orally administered in conjunction with the administration of collagen protein. As used in the preceding sentence, and elsewhere in this specification, "in conjunction with" (also referred to herein as in association with) means before, substantially simultaneously with or after oral administration of type II collagen protein. Naturally, administration of the conjoined substance should not precede nor follow administration of collagen by so long an interval of time that the relevant effects of the substance administered first have worn off. Therefore, synergists should usually be administered within about 24 hours before or after collagen protein and preferably within about one hour.

"Oral" administration includes oral, enteral or intragastric administration. Oral administration which does not bypass the stomach is preferred.

The present invention is based on the discovery and confirmation that oral administration of type II collagen in extremely low doses is a particularly effective means of treating and suppressing rheumatoid arthritis in humans. Thus, as demonstrated below, the oral administration of between 5 and 25 µg per day of type II collagen is an effective treatment for rheumatoid arthritis in humans. The compositions and methods of the invention do not have the drawbacks described above and associated with prior art therapeutic or palliative agents and techniques.

It has now been discovered that the preferred way to accomplish suppression of the immune responses against the human body's collagen in rheumatoid arthritis is the oral administration of purified or highly purified solubilized type II collagen protein in an amount between about 5 to about 25 µg and preferably 10–25 µg per day. The collagen useful in the present invention is type II collagen. Preferably, type II collagen that has been solubilized using known techniques is used in practicing the present invention. The solubilized collagen is prepared so that the resulting product is soluble at a physiologically acceptable acid pH. One such material is offered by Sigma Chemical Co. (St. Louis, Mo.) under the designation "Sigma Cell Culture Collagen Type II from Chicken Sternal Cartilage". The administration of collagen may be accomplished in a single dose form or multiple dose form. Preferably, the type II collagen protein is orally administered at a dosage of 20 µg per day.

In addition, synergists can be conjoined in the treatment to enhance the effectiveness of the type II collagen. Synergists are substances that bias an immune response towards the Th-2 type, i.e. cause T-cells to differentiate preferentially into Th-2-type T-cells. Non-limiting examples of synergists for use in the present invention include bacterial lipopolysaccharides from a wide variety of gram negative bacteria such as various subtypes of *E. coli* and Salmonella (LPS, Sigma Chemical Co., St. Louis, Mo.; Difco, Detroit, Mich.; BIOMOL Res. Labs., Plymouth, Pa.), Lipid A (Sigma Chemical Co., St. Louis, Mo.; ICN Biochemicals, Cleveland, Ohio; Polysciences, Inc., Warrington, Pa.) and immunoregulatory lipoproteins, such as peptides covalently linked to tripalmitoyl-S-glycarylcysteinyl-seryl-serine ($P_3C55$) which can be obtained as disclosed in Braun, V., *Biochim, Biophys, Acta* 435:-337, 1976. LPS is preferred and Lipid A particularly preferred. Lipid A is particularly preferred for use in the present invention because it is less toxic than the entire LPS molecule. LPS for use in the present invention can be extracted from gram negative bacteria and purified using the method of Galanes et al. (*Eur. J. Biochem.* 9:245, 1969) and Skelly, R. R., et al., (*Infect. Immun.* 23:287, 1979). Additional synergists that can be used in practicing the present invention are interferon Type I, interleukin-4 and interleukin-10 (as disclosed in PCT US95/04120 and PCT US95/04512, the disclosures of which are herein incorporated by reference and in their corresponding U.S. application Ser. Nos. 08/420,980 and 08/420,979).

Formulations

The present invention also includes oral pharmaceutical formulations and dosage forms comprising between about 5 and 25 µg and preferably 10 and 25 µg of type II collagen or acid-solubilized type II collagen in the form of a capsule, tablet, powder, or a liquid. Chicken type II collagen protein, soluble in water at acidic pH, can be obtained from commercial sources; (Sigma Chemical Company, St. Louis, Mo.) or can be purified according to the procedure of Trentham, D. et al., *J. Exp. Med.* 146:857, 1977. The formulations optionally further comprise a synergist as disclosed in the foregoing co-pending U.S. Patent Applications, in an amount effective (in conjunction with the tolerizing antigen of the present invention) to treat the clinical symptoms of arthritis. Synergists, when administered in conjunction with type II collagen, cause a further increase of suppressive cytokines such as PGE (prostaglandin-E), TGF-β, interleukin-4, and interleukin-10 in the vicinity of the collagen tissue under immune attack. Liquid aqueous formulations containing soluble type II collagen with an acid pH (e.g., type II collagen dissolved in 0.1M acetic acid) are preferred. The pH adjusting agent can be any pharmaceutically acceptable acidic agent and a buffer may also be included. The preferred pH range is 2.5 to 5.0. A solid composition can also be administered, preferably after it is dissolved in a pharmaceutically acceptable acidic aqueous medium such as 0.1M acetic acid.

Throughout this specification, it will be understood that any clinically or statistically significant attenuation of even one symptom of arthritis pursuant to the treatment of the present invention is within the scope of the invention. Such symptoms include joint tenderness (painful joints), joint swelling, AM stiffness, grip strength reduction, slowness in walking. In normal individuals, the first three aforementioned symptoms are absent, a 50-foot walk should take less than 9 seconds and adult strength should be more than 200 mm Hg (although strength varies with age, sex and physical condition). Clinically significant attenuation means perceptible to the patient (as in the case of tenderness or general well-being) and/or to the physician (as in the case of joint swelling). For example, a perceptible difference in swelling or tenderness in even one arthritic joint is significant. Absence of swelling or tenderness in a previously affected joint is most significant. For those parameters that are capable of measurement, a difference of 1 second in the case of the 50-foot walk, or 5 mm Hg in the case of strength or 15 minutes in AM stiffness is significant.

In addition, the ability to refrain from administration of cytotoxic drugs or other anti-inflammatory agents is also significant. Thus, even if the patient did not improve he/she is still deemed to have received a significant benefit of cytotoxic drugs and/or antiinflammatory agent administration did not have to resume, and the patient is kept in the same condition or progressive disease state as with these conventional drugs.

The type II collagen of the present invention is administered via the oral route in an oral dosage form. Suitable oral dosage forms include tablets, capsules, and powders. Liquid dosages comprising solutions or suspensions of 5–25 and preferably 10 to 25 µg of type II collagen (at a physiologically acceptable acid pH) can also be employed. Thus, one preferred embodiment comprises a pharmaceutically acceptable container holding 20 µg of type II collagen dissolved in 0.1M acetic acid which can be opened to permit the contents to be dispensed into orange juice or a similarly acidic juice to be ingested by the patient.

In addition to between 5 and 25 and preferably 10 and 25 µg of type II collagen, each oral formulation according to the present invention may comprise inert constituents including pharmaceutically acceptable carriers, diluents, fillers, solubilizing or emulsifying agents, and salts, as is well-known in the art. For example, tablets may be formulated in accordance with conventional procedures employing solid carriers well-known in the art. Capsules employed in the present invention may be made from any pharmaceutically acceptable material, such as gelatin, or cellulose derivatives. Sustained release oral delivery systems and/or enteric coatings for orally administered dosage forms are also contemplated, such as those described in U.S. Pat. No. 4,556,552, issued Dec. 3, 1985; U.S. Pat. No. 4,309,404, issued Jan. 5, 1982; and U.S. Pat. No. 4,309,406, issued Jan. 5, 1982.

Examples of solid carriers include starch, sugar, bentonite, silica, and other commonly used carriers. Further non-limiting examples of carriers and diluents which may be used in the formulations of the present invention include saline, syrup, dextrose, and water.

It will be appreciated that unit content of the active ingredient, type II collagen, contained in an individual dose of each dosage form need not in itself constitute an effective amount, since the necessary effective amount can be reached by administration of a plurality of dosage units (such as capsules or tablets or combinations thereof). Administration of an effective dosage may be in a single dose form or in multiple dosage forms and it may be provided with an enteric coating and/or a sustained release mechanism, such as a degradable matrix or a reservoir.

Where type II collagen is introduced orally or enterally, it may be mixed with other ingestible forms and consumed in solid, semi-solid solution, suspension, or emulsion form. It may also be mixed in conjunction or alternatively with pharmaceutically acceptable carriers, flavor enhancers, water, suspending agents and emulsifying agents.

The effective amount of a synergist, e.g., LPS or Lipid A, may be administered in conjunction with type II collagen, the amount of synergist being in the range of about 0.01 mg and 100 mg per day and preferably between about 0.1 mg and 10 mg per day.

T-cells from humans afflicted with rheumatoid arthritis can be collected from, e.g., peripheral blood and T-cells of the CD8+ type can be isolated and cloned. Those T-cells that secrete TGF-$\beta$, interleukin-4, or interleukin-10 in response to type II collagen can then be isolated, cloned, and used in an in vitro assay to test for their ability to secrete TGF-$\beta$ (and/or another suppressive cytokine) when stimulated by (in the presence of) a collagen peptide fragment. The ability of these cells to secrete TGF-$\beta$, interleukin-4 or interleukin-10, can be assessed e.g., by ELISA using commercially available monoclonal antibodies. The collagen peptide fragments that stimulate T-cells to secrete TGF-$\beta$, interleukin-4 or interleukin-10 will be orally tolerogenic. Such experiments have been described in U.S. patent application Ser. No. 843,752 filed Feb. 28, 1992, as well as in U.S. Patent application filed Jun. 5, 1995 in the names of Chen, Friedman, and Weiner entitled Use of Oral Tolerance to Suppress both the Th-1 and Th-2 Immune Responses and to Suppress Antibody Production. A method for isolating and cloning human T-cells has been described in U.S. patent application Ser. No. 502,559, filed Mar. 30, 1990 (and in corresponding PCT US91/02218), U.S. patent application Ser. No. 08/046,354 (and its corresponding PCT US93/03365), U.S. patent application Ser. No. 08/426,784 filed Apr. 20, 1995, and Allegretta, M., et al., *Science* 247:718–721, 1990.

The following example is intended to illustrate the present invention without limiting its scope.

EXAMPLE 1

For the purpose of the study conducted and described below, the patient's arthritic state was measured utilizing a combination of several different criteria such as subjective pain, gross anatomical observations, timing of physical acts and subjective well-being as described by the patient. Gross anatomical observations included AM stiffness, grip strength and number of swollen joints and were made during monthly examinations by a physician of the arthritic joints before and during type I collagen treatment as compared with the same joints prior to treatment.

Data measuring subjective pain involved applying gentle pressure to each arthritic joint in turn by a physician and being told by the patient whether pain was experienced.

Morning stiffness data were based on the patient's experience and reports on how long it took for their arthritic joints to become physically limber. Additionally, grip strength for each hand was measured each month with a standard mercury sphygmomanometer with the cuff inflated to 20 mm Hg. Finally, the patients were timed to measure how many seconds were needed to complete a 50-foot walk.

The efficacy of oral administration of type II collagen to humans afflicted with rheumatoid arthritis was evaluated using three different criteria: the Paulus Response Criteria, the American College of Rheumatology Criteria, and the Protocol Response Criteria. According to the Protocol Response Criteria, a positive response is scored when a $\geq 30\%$ improvement in tender and swollen joint counts is achieved in a subject.

In the American College of Rheumatology Response Criteria, a positive response is scored when:
a) a $\geq 20\%$ improvement in tender and swollen joint counts is achieved and
b) there is a $\geq 20\%$ improvement in any 3 of the following:
  (1) patient global score
  (2) physician global score
  (3) patient pain score
  (4) CLINHAQ (clinical health assessment questionnaire)
  (5) ESR (erythrocyte sedimentation rate)

A positive result is scored in the Paulus Response Criteria when 4 of the following 6 criteria are satisfied:
a) a $\geq 20\%$ improvement in
  (1) tender joint score
  (2) swollen joint score
  (3) duration of morning stiffness
  (4) ESR
b) a $\geq 40\%$ improvement in
  (5) physician global score
  (6) patient global score The "Intent to Treat" population included randomized patients for which any post-baseline efficacy data was obtained. If a patient in this group discontinued treatment, the response data for that patient was carried forward to succeeding time points in the study and used in calculating mean response values for a given group of subjects.

The "Per-Protocol" population is the population that completed the protocol, did not incur any significant protocol violations, exhibited at least 75% overall protocol compliance, did not take any proscribed medications for the duration of the protocol, and for whom it was not necessary to carry forward any data.

An "ever-response" subject is a participant in a clinical study of orally administered type II collagen who has ever shown a response to orally administered type II collagen, whether or not they completed the study or showed a long-term response.

Global assessment was subjectively made by the attending physician or the subject.

NSAID stands for "nonsteroidal antiinflammatory drugs"; RF stands for "rheumatoid factor"; ESR stands for "erythrocyte sedimentation rate"; HCT stands for "hematocrit";

bid stands for "twice a day"; qid and qd stand for "per day"; IA stands for "intra-joint".

This study involved 274 patients with severe, active rheumatoid arthritis. The mean duration of disease in the patients in the study was 11.2 years. At entry, patients had a mean of 24 swollen and 27 tender joints. One hundred twenty-four (45%) of the patients were being treated with disease-modifying anti-rheumatoid drugs (DMARDS) and were taken off DMARD medication for an 8–12 week period (depending on which DMARD was used). For methotrexate, immunosuppressants and intraarticular steroids, the washout period was 8 weeks. For all other DMARDS and/or other investigational anti-rheumatic therapy, the washout period was 12 weeks. Stable doses of non-steroidal anti-inflammatory drugs (NSAIDS) and oral corticosteroids (<10 mg per day) were permitted. Subjects were randomly assigned to receive either placebo or type II collagen at 20, 100, 500, or 2,500 µg per day. There were between 53–57 patients in each of the five groups. There were no statistically or clinically relevant differences between treatment groups. A total of 228 patients (83%) completed the full six month treatment period. The frequency of dropouts was similar across all treatment groups.

FIG. 1 illustrates the relative efficacy of the various dosage amounts of type II collagen over the 24 week treatment period. At 24 weeks, the percentage of subjects receiving the 20 µg per day dose who were responding to treatment was higher than the number of placebo-receiving subjects in response, but the difference at the 24 week point is not significant.

However, in Table 1 below it is shown that 39% of the ever-response subjects showed a response to 20 µg per day type II collagen treatment vs. 19% of the placebo-receiving subjects. Thus, responses significantly greater than responses from placebo treatment were seen with the 20 µg per day dose using the Paulus criteria. A linear logistic regression analysis of ever-response subjects, which controls for rescue analgesia, NSAIDS, and corticosteroid use by the subjects, yielded a P-value of 0.02 when comparing the response elicited by 20 µg per day type II collagen against placebo, substantiating the significant difference found between the number of subjects responding to 20 µg per day and placebo.

TABLE 1

Dose Ranging Placebo Controlled Study of Oral CCII in Rheumatoid Arthritis
Response Rates by Treatment Group
Intent-to-Treat Population

| Ever Response | | Treatment Group | | | | | | | | |
|---|---|---|---|---|---|---|---|---|---|---|
| | | Placebo (N = 57) | | 0.02 mg/day (N = 54) | | 0.10 mg/day (N = 55) | | 0.50 mg/day (N = 53) | | 2.50 mg/day (N = 54) |
| | | N | % | N | % | N | % | N | % | N | % |
| Paulus | Response Rate | 16 | 19.3 | 25 | 38.9 | 19 | 32.7 | 17 | 28.3 | 13 | 24.1 |
| | P-value* | | — | | 0.0353 | | 0.1323 | | 0.3693 | | 0.6462 |
| ACR | Response Rate | 11 | 17.5 | 14 | 25.9 | 11 | 20.0 | 13 | 24.5 | 12 | 22.2 |
| | P-value* | | — | | 0.3579 | | 0.8112 | | 0.4824 | | 0.6360 |
| Protocol | Response Rate | 18 | 31.6 | 25 | 46.3 | 22 | 40.0 | 23 | 43.4 | 22 | 40.7 |
| | P-value* | | — | | 0.1234 | | 0.4311 | | 0.2386 | | 0.3306 |

*Fisher's exact test comparing active treatment groups to placebo

Type II collagen, derived from chicken sternum, was obtained from the Sigma Chemical Company, St. Louis, Mo. Patients were provided with a one month supply of blinded study medication at the baseline visit and every four weeks thereafter. Liquid study medication was provided in the form of patient kits containing each daily dose in individual polystyrene tubes. The study medication required refrigeration so patients were given coolers to transport the medication home and were instructed to keep the kits in the refrigerator. Clinical trial material was administered orally once a day. The daily dose consisted of a single liquid filled tube containing 0.1M acetic acid (placebo) or type II collagen dissolved in 0.1M acetic acid which was added by the subject to orange juice (or other acidic juice) and was taken at least 20 minutes before breakfast.

The protocols required subject examination by a physician of each subject participating in the study at 2, 4, 8, 12, 16, 20, and 24 weeks from the baseline date (date of entry into the study). During each examination the physician evaluated the subject for the criteria included in the Paulus Response, the American College of Rheumatology Response, and the Protocol Response evaluations. The physicians recorded the data, which were then collated and subjected to statistical analyses. The data collected in the study are reported in Table 1 and FIGS. 1–3.

Figure 2:
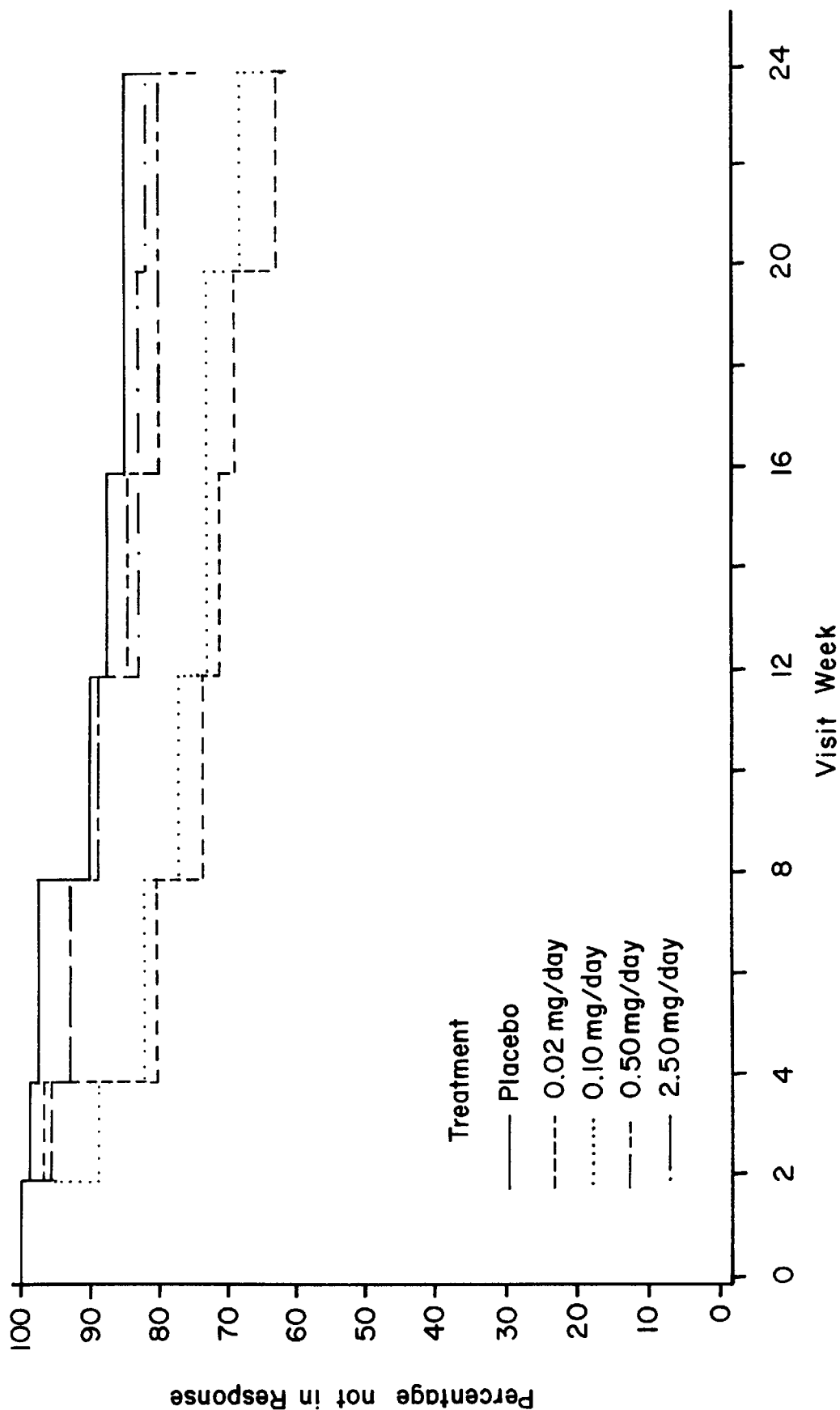
FIG. 2 is a graph which shows the percentage of subjects not in response to treatment with a range of doses of type II collagen in the Intent-to-Treat population over a period of 24 weeks.

The 20 µg per day dose of type II collagen also showed a significant advantage in terms of time to response compared with placebo (P=0.03). Graphical representation of the time to response elicited by different dosages is shown in FIG. 2, where it can be seen that the 20 µg per day dose elicits a faster time to response than does placebo.

Figure 3:
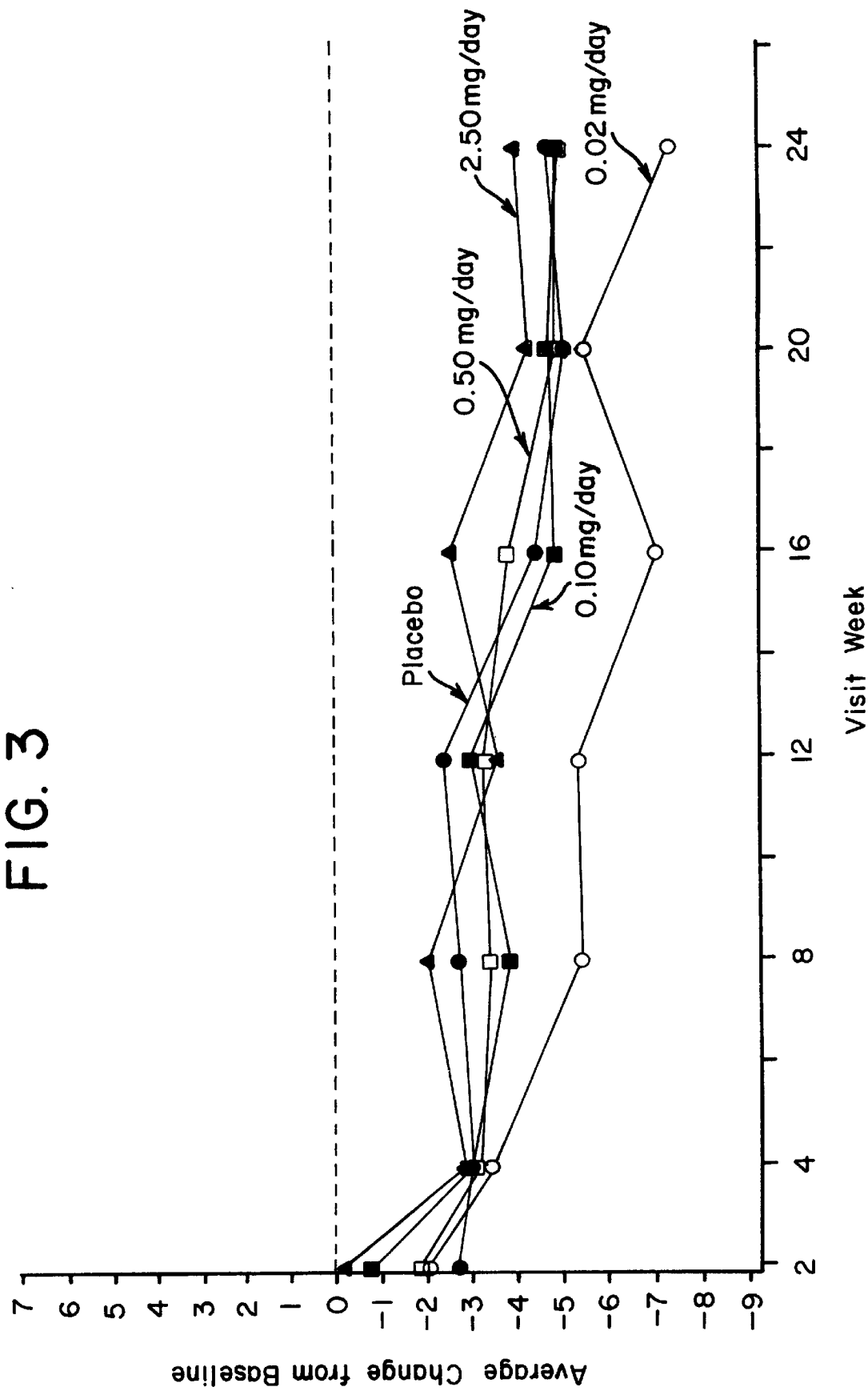
FIG. 3 is a graph which shows the average change from baseline in tender joint counts in response to a range of doses of type II collagen in the Intent-to-Treat population over a period of 24 weeks.
Figure 4:
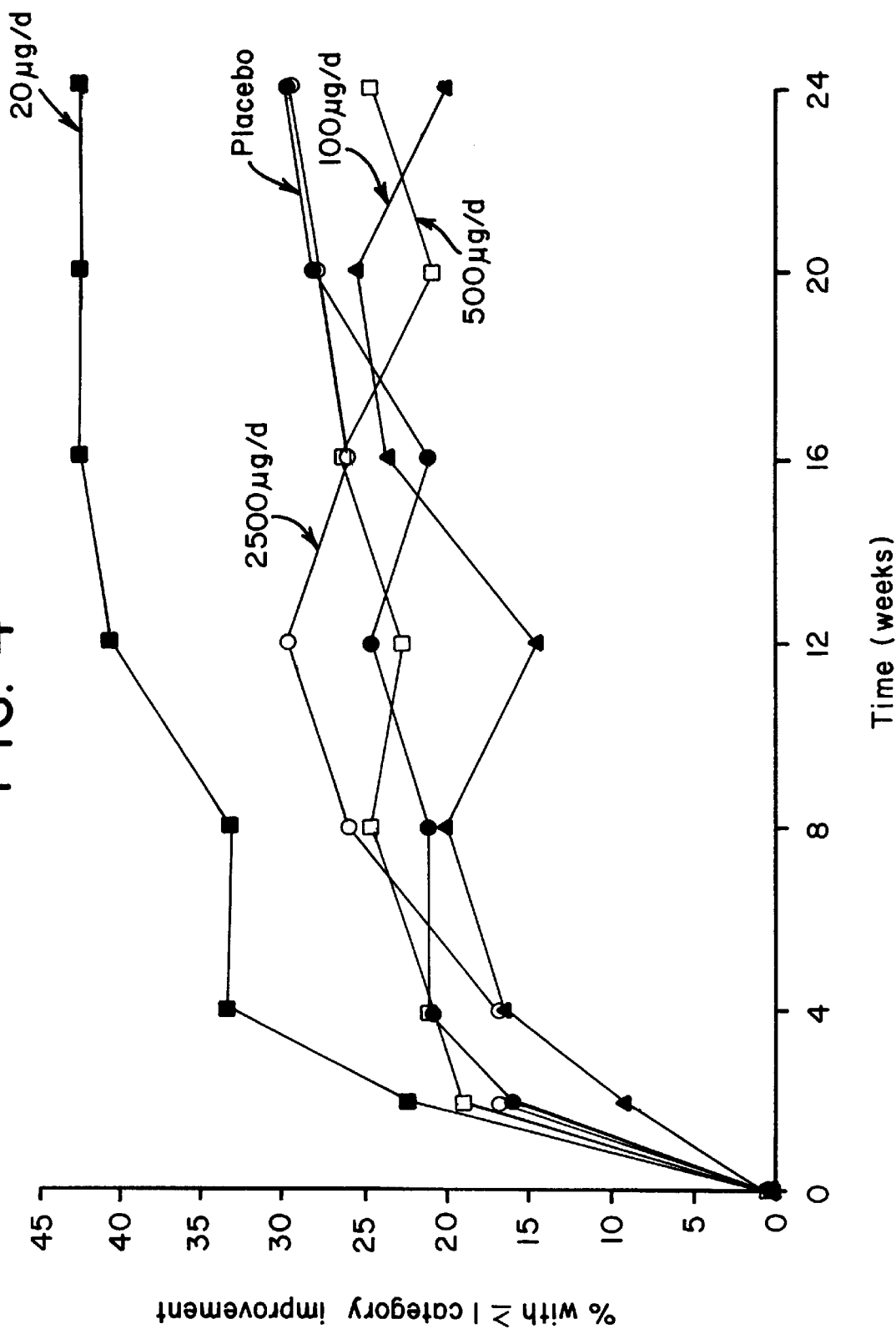
FIG. 4 is a graph which shows the percent improvement in Physician Global Score in subjects treated with a range of doses of type II collagen in the Intent-to-Treat population over a period of 24 weeks.
Figure 5:
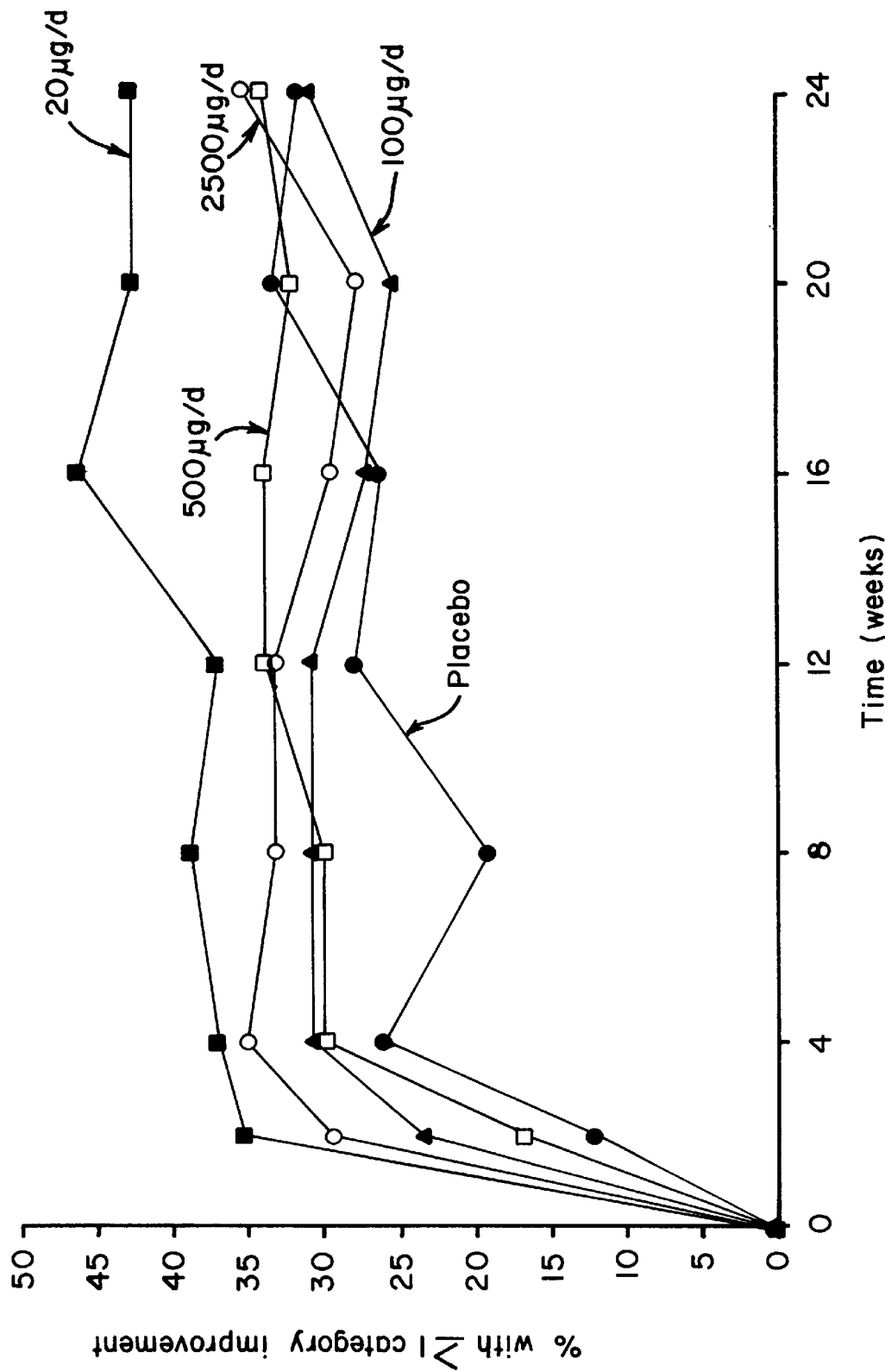
FIG. 5 is a graph which shows the percent improvement in Patient Global Score in subjects treated with a range of doses of type II collagen in the Intent-to-Treat population over a period of 24 weeks.

FIG. 3 shows the average change from baseline in subject groups taking the range of type II collagen doses. The 20 µg per day dose elicited the greatest absolute reduction in tender joint count, but is was not significantly different from placebo. It was, however, significantly different from the baseline tender joint count. Similarly, the 20 µg per day dose achieved significant improvement from baseline in the Physician Global Assessment (FIG. 4) and Patient Global Assessment (FIG. 5) of disease activity, although these results were not significantly different from placebo. In addition, there are clear numeric trends in favor of the 20 µg per day treatment group versus the other treatment groups for tender joint count and Physician and Patient Global Assessments.

Thus, this study has shown the 20 µg per day dose of type II collagen to have significant advantages over higher dose levels in the treatment of rheumatoid arthritis. This dose showed a significant advantage over placebo using the Paulus criteria ever-response rates, and elicited the highest ever-response rates among the 4 dose levels employed in the study. Of all the dosages used, the 20 μg per day dose elicited the best improvements from baseline for the following efficacy measures: tender joint counts, swollen joint counts, physician global scores, patient global scores, patient pain scores, and ESRs. The 20 μg per day dose also resulted in the earliest time-to-response, using the Paulus criteria.

With regard to safety, no serious adverse events were noted which were judged related to clinical trial material. There was no difference among any dose of type II collagen or placebo with respect to reported adverse events. The high completion rate (83%) of patients enrolled attests to the tolerability of Type II collagen.

EXAMPLE 2

Extended Therapy of Rheumatoid Arthritis Patients with Type II Collagen

Approximately 140 of the original 274 severely arthritic patients (i.e. patients with greater than 24 swollen or tender joints) participating in the study of Example 1 have continued receiving Type II collagen via the oral route for between 18 months and 2 years. Of these patients, 126 receive 20 μg per day in a single dose. The arthritic symptoms of these patients have been controlled by the 20 μg per day dose. Fourteen of the patients who have continued on Type II collagen therapy required higher doses, and were titrated to a dosage of 100 μg per day. All of the patients continuing in the study have gone for between 18 months and 2 years without receiving any disease modifying anti-rheumatoid drugs (DMARDS), such as methotrexate, immunosuppressants, and intraarticular steroid injections. Thus, oral therapy with Type II collagen at 20 μg per day has provided satisfactory treatment for rheumatoid arthritis in these severely afflicted patients for 18 months or more.

What is claimed is:

1. A method for treating rheumatoid arthritis in humans which comprises orally administering between about 5 to 25 μg per day of type II collagen to a human in need of such treatment, for a period of time sufficient to decrease at least one clinical symptom selected from the group consisting of joint tenderness, joint swelling, morning stiffness, grip strength, and 50-foot walk time.

2. The method of claim 1 which comprises administering about 20 μg per day of type II collagen to said human.

3. The method of claim 1 wherein said type II collagen is dissolved in a physiologically acceptable aqueous acidic medium.

4. A method of treating at least one arthritis symptom in a human in need of such treatment which comprises orally administering to said human between 5 and 25 μg per day of type II collagen.

5. A method of treating at least one arthritis symptom in a human in need of such treatment which comprises orally administering to said human about 20 μg per day of type II collagen.

6. A method of suppressing an autoimmune response in at least one afflicted joint in a human in need of such treatment which comprises orally administering to said human between about 5 to 25 μg per day of type II collagen.

7. A method of suppressing an autoimmune response in at least one afflicted joint in a human in need of such treatment as defined in claim 6 which comprises orally administering to said human about 20 μg per day of type II collagen.

8. A dosage form for use in treating rheumatoid arthritis in humans comprising a pharmaceutically acceptable container holding between 5 and 25 μg of type II collagen dissolved in a physiologically acceptable acid.

9. The method of claim 1, wherein the amount of collagen administered is between 10 and 25 μg per day.

10. The method of claim 4, wherein the amount of collagen administered is between 10 and 25 μg per day.

11. The method of claim 6, wherein the amount of collagen administered is between 10 and 25 μg per day.

12. The dosage form of claim 8 wherein the amount of collagen is between 10 and 25 μg.

* * * * *